US006574482B1

(12) United States Patent
Radomsky et al.

(10) Patent No.: US 6,574,482 B1
(45) Date of Patent: Jun. 3, 2003

(54) DUAL RF/IR COMMUNICATION DEVICE AND METHOD OF USE THEREOF

(75) Inventors: Israel Radomsky, Herzetia (IL); Israel Abrams, Kfar Saba (IL); Yossef Bruslavsky, Raanana (IL)

(73) Assignee: Elpas Electro-Optic Systems Ltd., Raanana (IL)

( * ) Notice: Subject to any disclaimer, the term of this patent is extended or adjusted under 35 U.S.C. 154(b) by 0 days.

(21) Appl. No.: 09/434,716

(22) Filed: Nov. 5, 1999

(51) Int. Cl.$^7$ .............................................. H04B 14/04
(52) U.S. Cl. ................. 455/517; 455/150.1; 455/151.1; 455/151.2; 455/456; 379/56.3
(58) Field of Search ........................... 455/150.1, 151.1, 455/151.2, 151.4, 903, 550, 456; 340/573.4, 572.1, 825.36, 825.39, 825.71, 825.72, 825.49; 379/56.1, 56.2, 56.3; 359/109, 155, 152

(56) References Cited

U.S. PATENT DOCUMENTS

| | | | |
|---|---|---|---|
| 5,257,288 A | * | 10/1993 | Moser |
| 5,301,353 A | * | 4/1994 | Borras et al. ................. 340/539 |
| 5,515,426 A | * | 5/1996 | Yacenda et al. .............. 379/201 |
| 5,608,723 A | * | 3/1997 | Felsenstein ................... 370/335 |
| 5,636,266 A | * | 6/1997 | Ranganath et al. ........... 379/58 |
| 5,745,272 A | | 4/1998 | Shipley |
| 5,880,867 A | * | 3/1999 | Ronald ........................ 359/152 |
| 5,880,868 A | * | 3/1999 | Mahany ....................... 359/152 |
| 5,886,634 A | * | 3/1999 | Muhme ........................ 340/572 |
| 5,917,425 A | * | 6/1999 | Crimmins et al. ...... 340/825.49 |
| 5,977,913 A | * | 11/1999 | Christ ............................ 342/2 |
| 6,011,487 A | * | 1/2000 | Plocher .................. 340/825.49 |
| 6,154,139 A | * | 11/2000 | Heller ...................... 340/573.4 |
| 6,161,005 A | * | 12/2000 | PinZon ........................ 455/403 |
| 6,175,308 B1 | * | 1/2001 | Tallman et al. ............. 340/539 |

FOREIGN PATENT DOCUMENTS

WO  WO 96/31021  10/1996

OTHER PUBLICATIONS

Martin, Brian W., "Watchit. A Fully Supervised Identification, Location and Tracking System." Proceedings of the Annual International Carnahan Conference on Security Technology, US, New York, IEEE, vol. Conf. 29, Oct. 18, 1995, pp. 306–310, XP000585871.

* cited by examiner

*Primary Examiner*—William Trost
*Assistant Examiner*—Congvan Tran
(74) *Attorney, Agent, or Firm*—Browdy and Neimark, P.L.L.C.

(57) ABSTRACT

A communication device including an RF transmitter mounted in conjunction with an IR transmitter allowing data to be transmitted by RF as well as by IR. Such a device may be a portable badge worn by moving personnel to transmit IR and RF signals to one of a plurality of second devices each being a fixed reader having an IR and RF receiver, and typically being mounted in a respective enclosed space, such as a room. In use, IR transmissions from the portable device are detected by the IR receiver of the reader in the same room and thus provide an immediate identification of the room (or enclosed space) wherein the portable device is located. On the other hand, if the IR transmitter in the portable device is concealed or for any other reason is not within line-of-sight of the reader in its immediate proximity, then the RF signal transmitted by the RF transmitter in the portable device is detected by the RF receiver in the reader, thereby allowing tracking of the portable device in either eventuality.

25 Claims, 18 Drawing Sheets

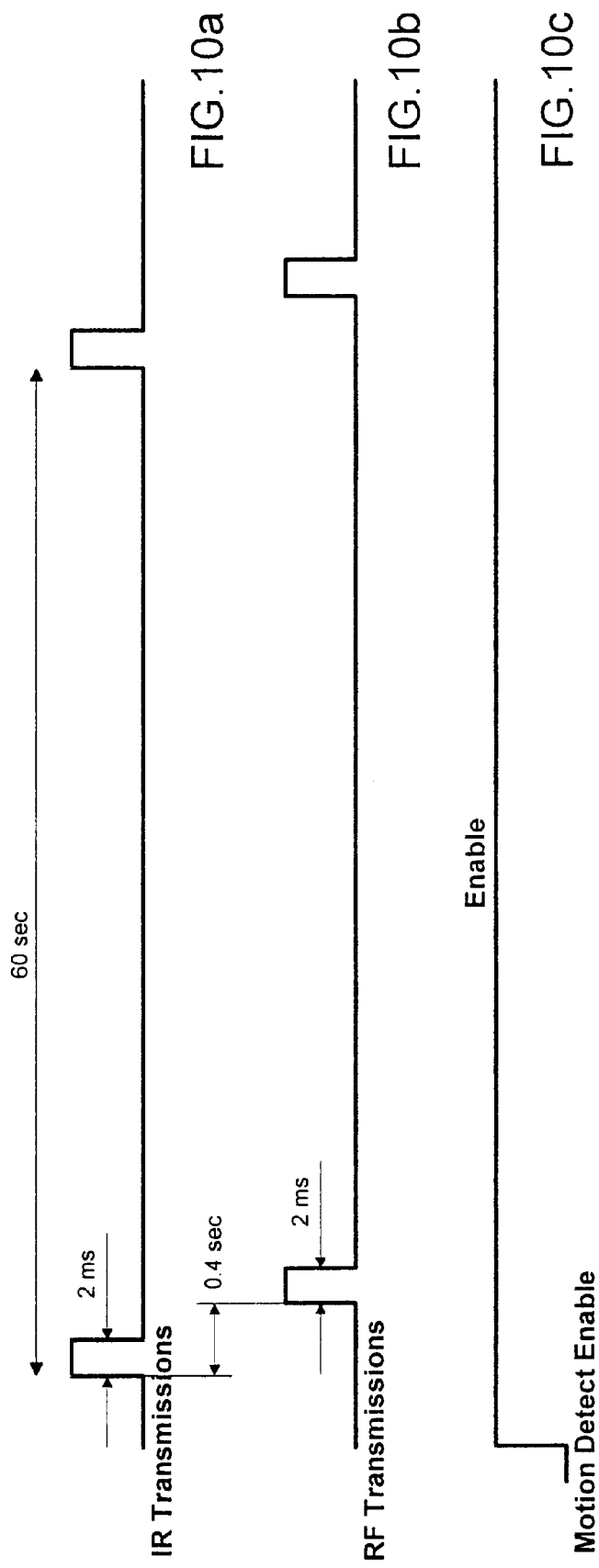

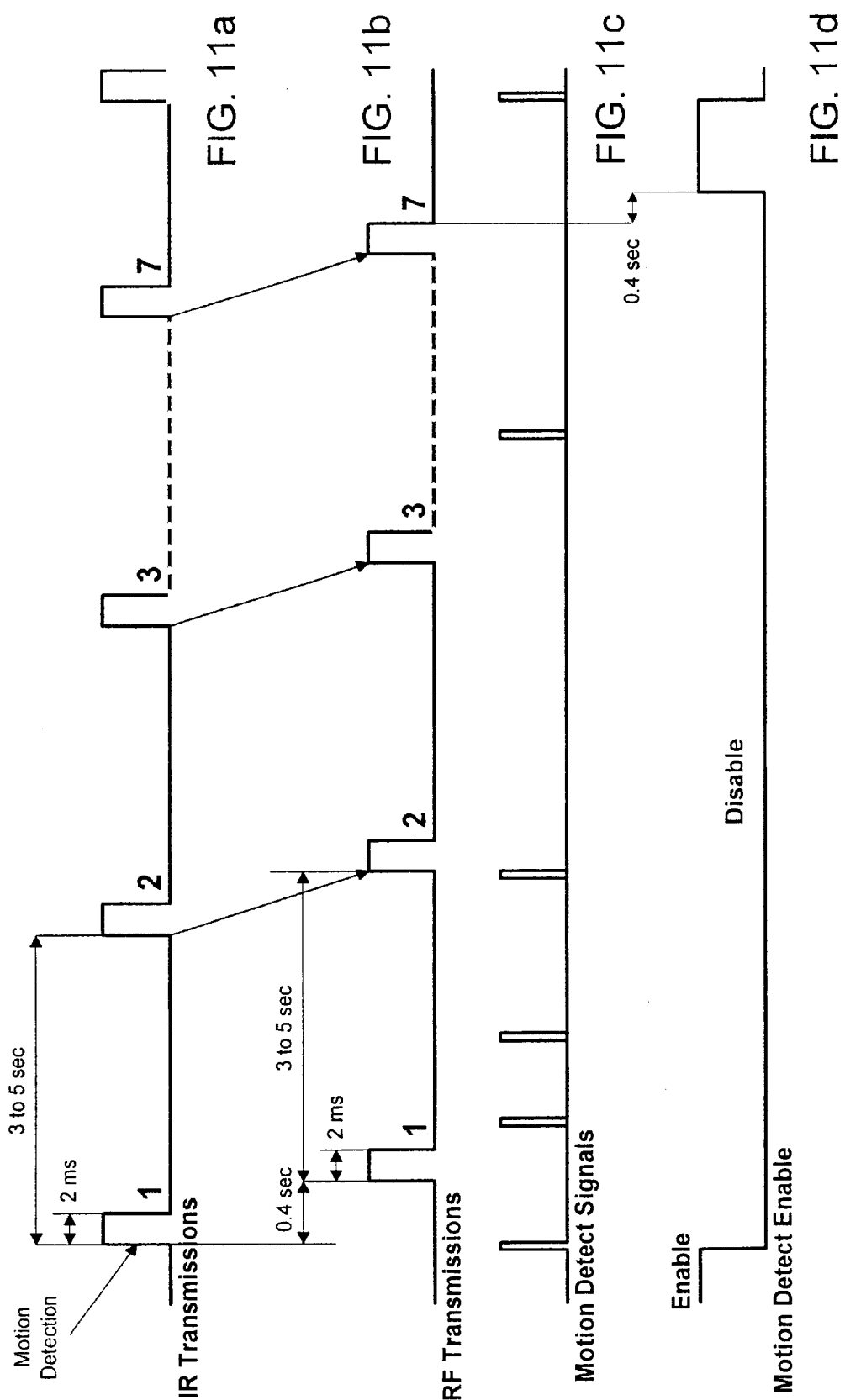

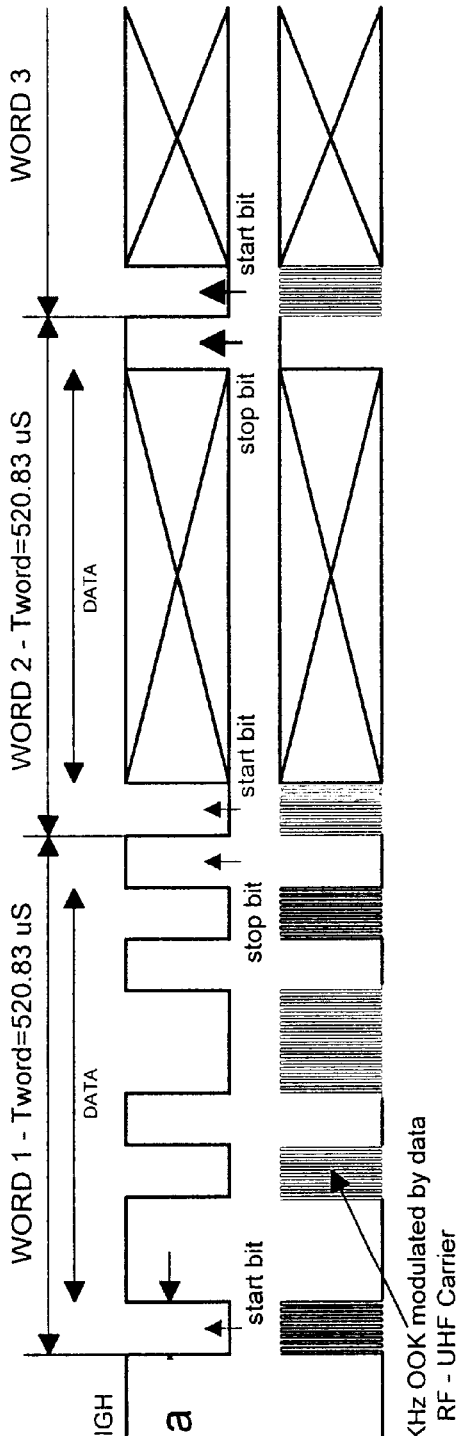
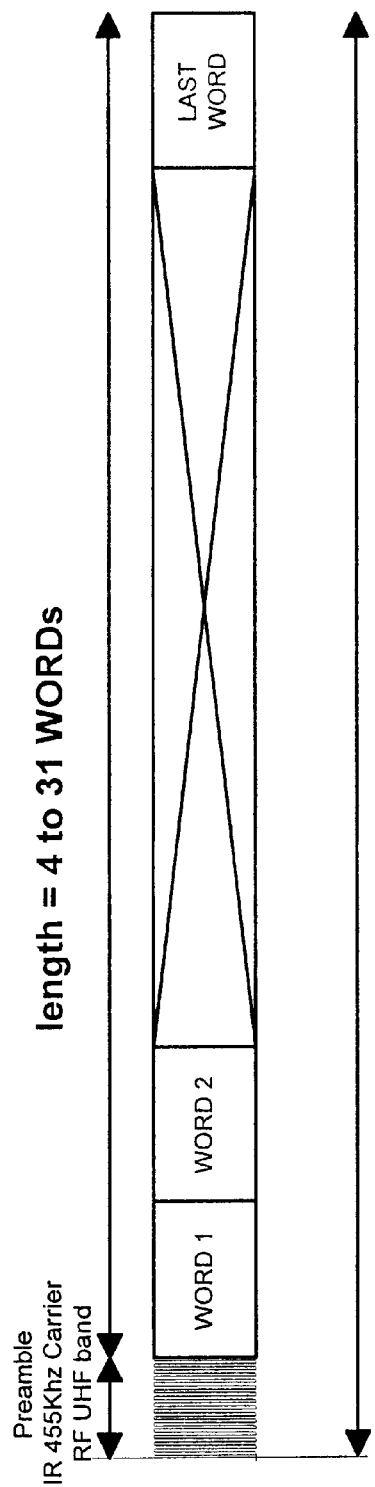
FIG. 12a
FIG. 12b
FIG. 12c

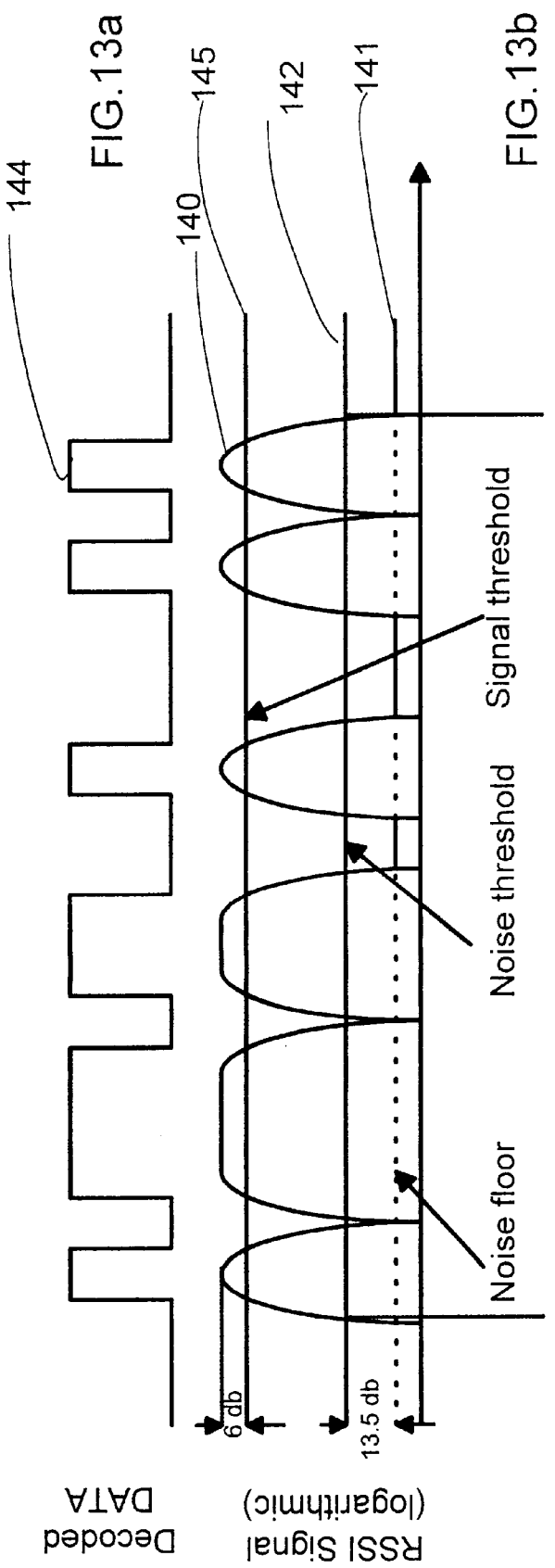

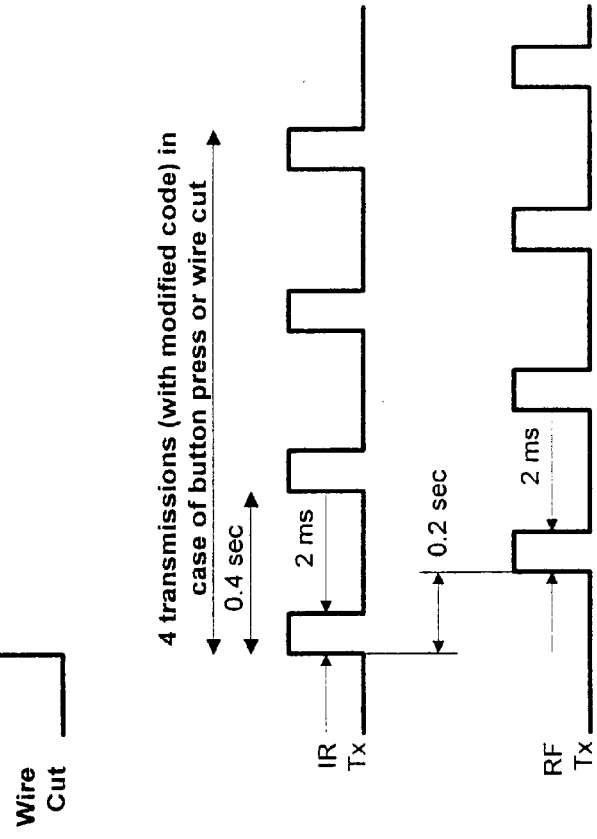
FIG.14a Button Press
FIG.14b Wire Cut
FIG.14c IR Tx
FIG.14d RF Tx
In case of wire cut - modified code
Every 4-5 sec
Every 4-5 sec
4 transmissions (with modified code) in case of button press or wire cut
0.4 sec
2 ms
0.2 sec
2 ms

US 6,574,482 B1

DUAL RF/IR COMMUNICATION DEVICE AND METHOD OF USE THEREOF

FIELD OF THE INVENTION

This invention relates to low-power, particularly battery-operated, RF and IR transmitters.

BACKGROUND OF THE INVENTION

Unlike infra-red (IR) transmitters which require a direct line-of-sight with their respective receivers, RF transmitters have the advantage that no such direct line-of-sight is required. On the other hand, IR transmitters are becoming increasingly popular owing to their small size and their ability to handle ever-increasing volumes of data traffic at high speed. Remote controls for television and the like based on IR detectors are, of course, well known but there is an increasing tendency to employ IR transmitters as personal data badges for a variety of applications. Such applications include access control utilities: not only for gaining access to protected territory but, no less importantly, for maintaining constant supervision and monitoring of a person's location.

One specific application where such a requirement is mandatory elates to the monitoring of patients in a hospital. A patient is frequently instructed to present himself at one or more departments within the hospital for the purpose of various examinations such as, for example, X-rays, ultrasound and so on. During this routine, the patient is obviously unsupervised and generally makes his own way from one department to another. Notwithstanding that this procedure is common, it is fraught with danger and insecurity. There is the obvious risk that, owing to confusion on the part of the patient, he may go to the wrong department, thereby at best wasting significant amounts of time if not undergoing unnecessary tests. There is also the risk that the patient may leave the hospital without having had the necessary tests and that, in consequence, further diagnosis of the patient may be aborted with possibly catastrophic results.

The use of IR detectors for monitoring the whereabouts of moving people is known per se. Therefore, one possible solution to the scenario set out above would be to provide each patient with an IR identity tag, whereupon his progress throughout the hospital could be monitored. However, it is not uncommon for patients, unthinkingly, to put their identity badge inside a pocket or purse. In this case the patient is effectively "lost" from view because the IR transmitter within the identity badge requires direct line of sight with the receiver and there is no way in which the IR signal can penetrate the patient's pocket or purse. Obviously, should this occur, the patient's apparent loss will immediately be inferred and steps may then be taken by the hospital's security staff to locate him. However, this is a cumbersome procedure and increases the already overstretched burden of the hospital's security staff. Moreover, of course, if the patient succeeds in leaving the boundaries of the hospital, then locating the patient in order to retrieve the missing badge becomes even more difficult; and if, moreover, the patient's health suffers as a result, then the hospital may be held criminally negligent.

Similar considerations apply to the use of IR badges for tracking babies in order to prevent theft from maternity wards. In this case, it is also necessary to safeguard against a thief merely removing the IR badge prior to abduction. This may be achieved by typing the badge to the baby using an electrically conductive wire and then monitoring the electrical continuity of the wire.

A further drawback with the use of IR badges for location tracking is that accurate location is dependent on dividing an area into independent units each having an IR reader for communicating with an IR badge within its respective reception coverage. By such means, it is easy to determine which reader is in line of sight contact with a particular badge and thereby infer the location of the badge. This, however, has tended to militate against the use of IR badges for tracking location in wide open spaces.

There is thus clearly a need to allow for constant monitoring of a patient within a hospital in both confined and open spaces whilst, at the same time, protecting both the patient and the hospital management against his apparent disappearing owing to the mis-location of a conventional IR identity tag.

The use of an RF transmitter for this purpose would obviously go a long way to solving such a problem. However, RF transmitters are subject to problems of their own, including the need to secure approval by the requisite Communications Authority. Moreover, the use of an RF-only system for the purpose of location and identification is not feasible, because RF transmission crosses walls, ceilings and floors, thus militating against exact and precise determination (per room or enclosed area) of the location of the RF transmitter.

SUMMARY OF THE INVENTION

It is therefore an object of the invention to provide a low-powered RF transmitter in which the above-mentioned drawbacks are significantly reduced or eliminated.

It is a particular object of the invention to provide an RF transmitter for mounting in conjunction with an IR transceiver so as to allow for the data to be transmitted by RF as well as by IR within a single battery-operated portable module.

Yet another object of the invention is to provide such an RF transmitter which transmits a substantially constant energy pulse regardless of battery drainage.

These objects are realized in accordance with a broad aspect of the invention by a communication device including an RF transmitter mounted in conjunction with an IR transmitter allowing data to be transmitted by RF as well as by IR.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIGS. 10a to 10c show timing diagrams of IR and RF transmissions and a motion detect enable signal;

FIGS. 11a to 11d show timing diagrams of IR and RF transmissions, motion detect and motion detect enable signals after motion detection;

FIGS. 12a and 12b show timing diagrams of a suitable IR/RF modulation scheme;

FIG. 12c shows pictorially a detail of a suitable IR/RF transmission protocol;

FIGS. 13a and 13b are timing diagrams of a data decoding circuit for use in the IR/RF receiver of the badge;

FIGS. 14a to 14d are timing diagrams relating to button press and wire cut functions of the badge;

DETAILED DESCRIPTION OF A PREFERRED EMBODIMENT

Figure 1:
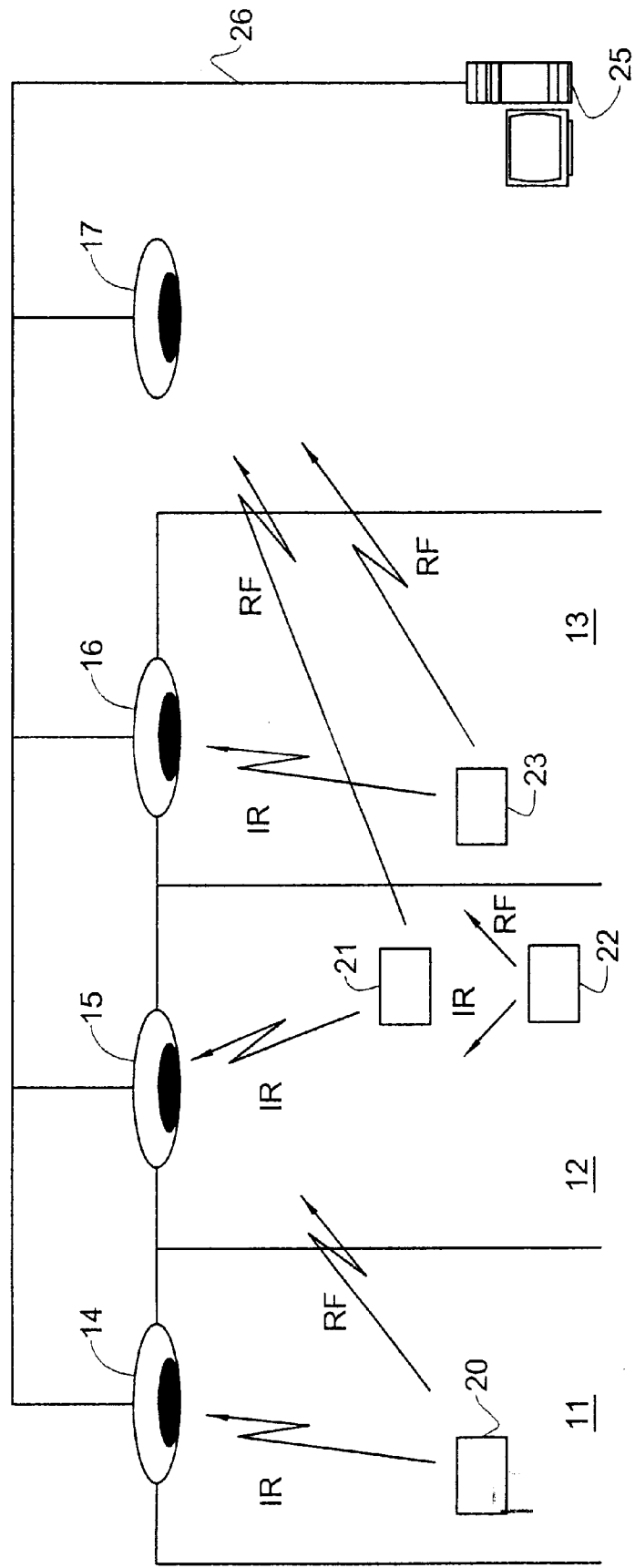
FIG. 1 is a pictorial representation of an IR/RF location system employing IR/RF badges according to the invention.

FIG. 1 shows in plan view a pictorial representation of a geographical area depicted generally as 10 comprising three separate and mutually adjacent rooms 11, 12 and 13. In each of the three rooms 11 to 13 there is mounted on the ceiling a corresponding IR reader 14, 15 and 16 constituting a location transceiver which allows transmission and reception of data using IR transmission. Also provided is an RF reader 17 providing RF coverage for the zone containing the three rooms 11 to 13. Portable IR/RF badges 20, 21, 22 and 23 as well as a portable IR badge 24 are worn by moving objects or people for mobility between the three rooms. The IR/RF badges 20 to 23 constitute object transceivers, which can transmit IR data to an unobstructed IR reader as well as RF data to the RF reader 17 in addition to receiving data therefrom. In contrast thereto, the IR badge 18, which also constitutes an object transceiver, can send only IR data to an unobstructed IR reader. A server 25 is connected to the three IR readers 14, 15 and 16 as well as to the RF reader 17 via a LONTALK network 26 and is responsive to signals generated by the IR and RF readers 14, 15, 16 and 17 for reception and monitoring the transmissions of the IR and RF badges. LONTALK is a registered trademark of the Echelon Corporation. If a door (not shown) between the two rooms 11 and 12 be ajar, then an IR signal transmitted by the reader 14 so as to detect the IR/RF badge 20 within the room 11 can pass through the open door into the adjacent room 12 and thus, incorrectly, read the objects therein. Likewise, the reader 15 can incorrectly read objects within the room 11 if the door between the two rooms is open. On the other hand, for so long as the door between adjacent rooms is closed, then the room constitutes a closed zone, whose identification uniquely determines the location of an IR transmitter therein.

Figure 2:
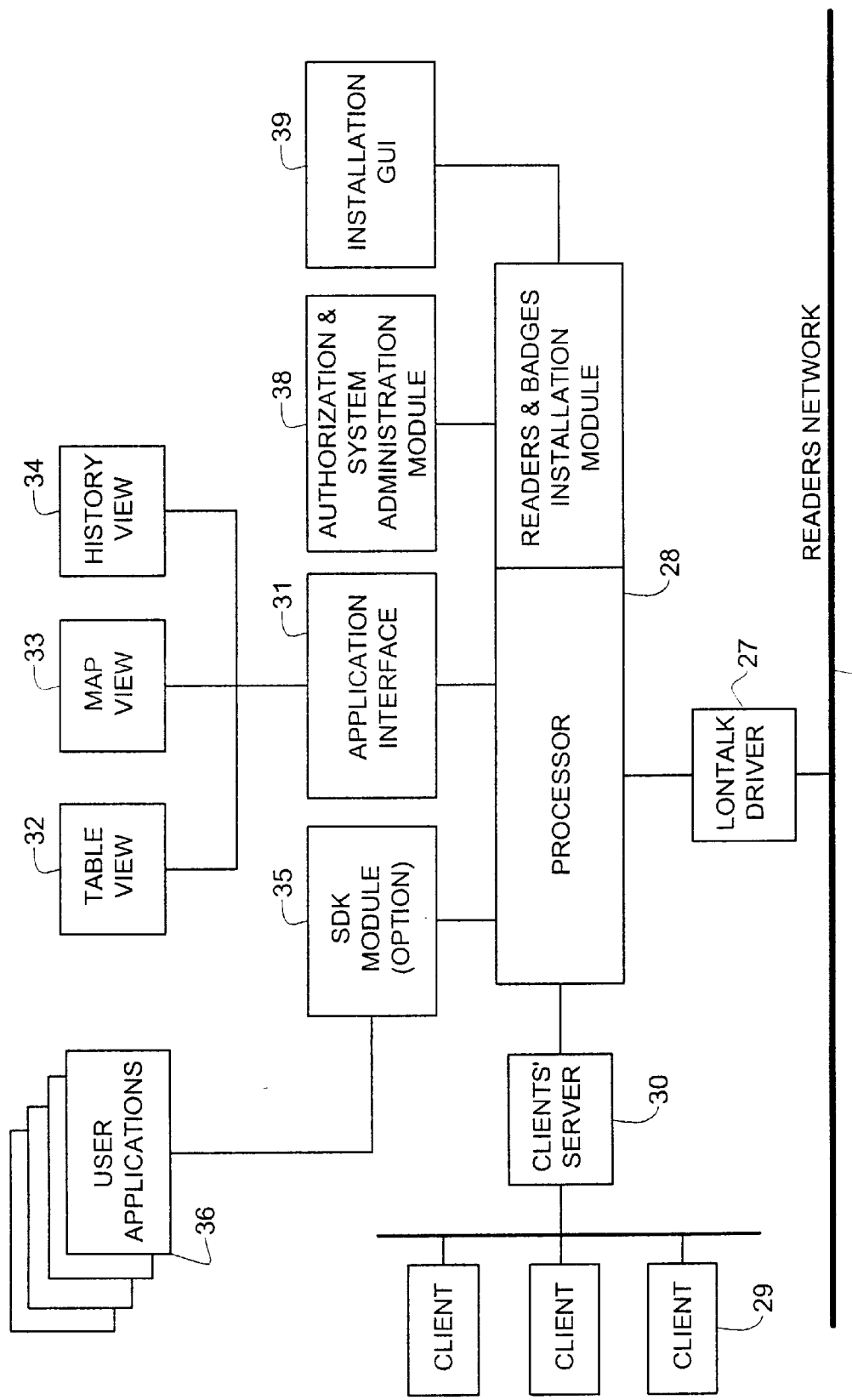
FIG. 2 is a block diagram showing functionally the software modules associated with IR/RF location system depicted in FIG. 1.

FIG. 2 shows functionally the various software modules associated with IR/RF location system 10. The readers 14 to 17 are interconnected by the LONTALK network 26 via a driver 27 to a processor 28 which processes data transmitted by the badges and the RSSI data and noise signals generated in the readers 14 to 17, and determines location and motion of the badges. End-users or clients 29 are networked and connected to the processor 28 by a client server 30. The clients 29 are provided with display monitors (not shown) for viewing location data depicting movement of the badges throughout the zone covered by the readers 14 to 17. Such location data may be represented in different formats such as, for example, tabular form, map view and showing the movement history of a specific badge. To this end, the processor 28 is coupled, via an application interface 31 to different software modules 32, 33 and 34 corresponding respectively to each of these formats for formatting the data in the required manner for viewing by the different clients 29.

An optional Software Developer's Kit (SDK) module 35 may be connected to the processor 28 and allows development by, or behalf of, the clients 29 of customized user applications 36. A readers and badges installation module 37 coupled to the processor 28 allows new badges and readers to be installed and is coupled to an authorization and administration module 38 and installation GUI 39. The authorization and administration module 38 ensures that only authorized personnel are permitted to assign and install new badges, whilst the installation GUI 39 provides a graphical interface for facilitating such installation.

Figure 3:
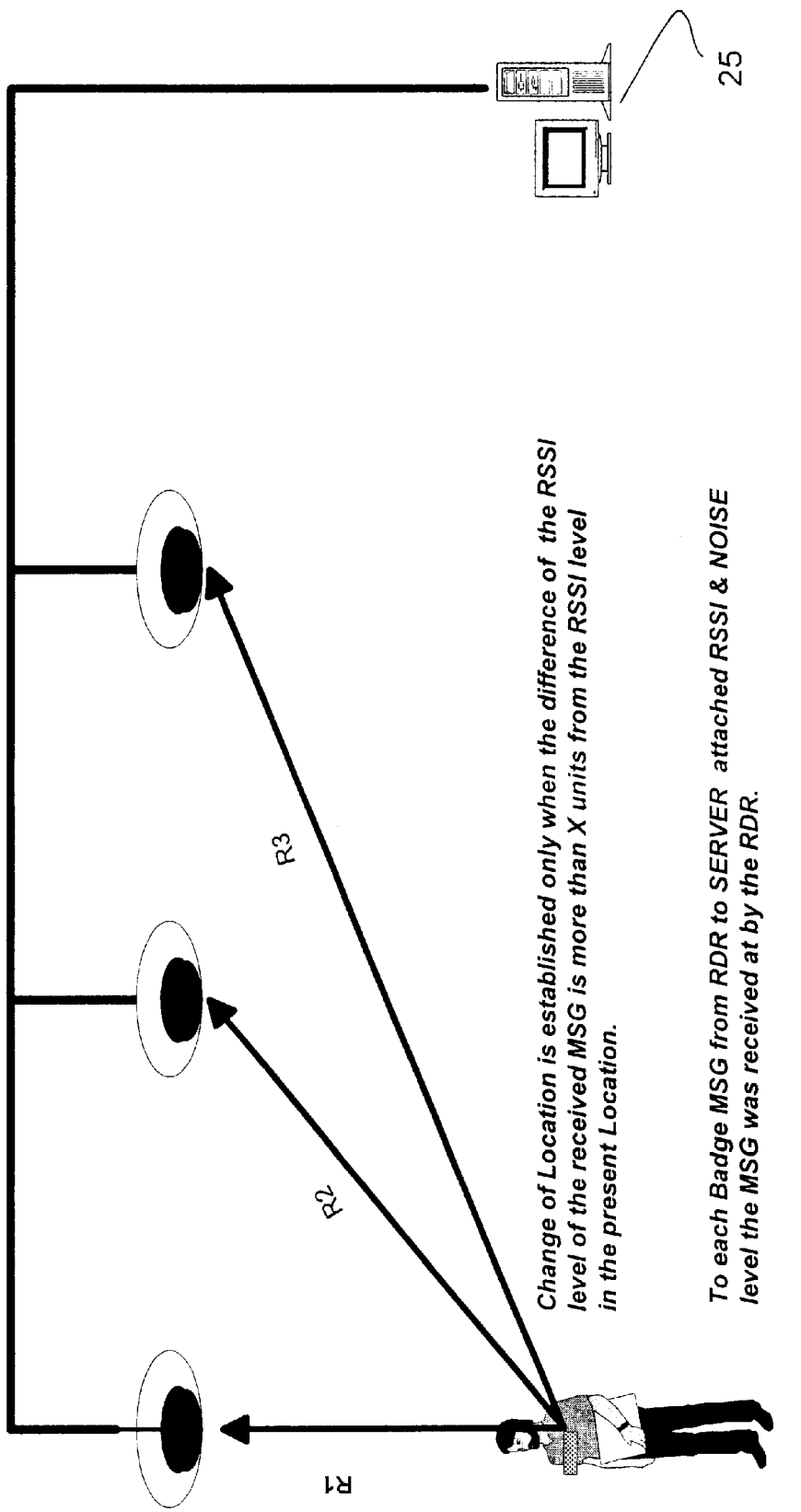
FIG. 3 is a pictorial representation showing how a server in the IR/RF location system determines badge location in open space.

FIG. 3 shows pictorially the manner in which the server 25 determines movement of a badge as well as its location in open space such that more than one IR reader can receive IR signals transmitted by the badge. In the first instance, movement is inferred based on a change in strength of the signal received by the corresponding IR or RF reader. To this end, each of the IR readers includes a decoder having a Received Signal Strength Indicator (RSSI) for determining the signal strength of the received signal. When the signal strength of a received message varies by more than a predetermined threshold from the RSSI level in the present location, this is taken as an indication that the badge has moved location from one room to another. When several messages are received by the server 25 from a single badge, the badge's location is determined from the message with the highest RSSI.

Figure 4:
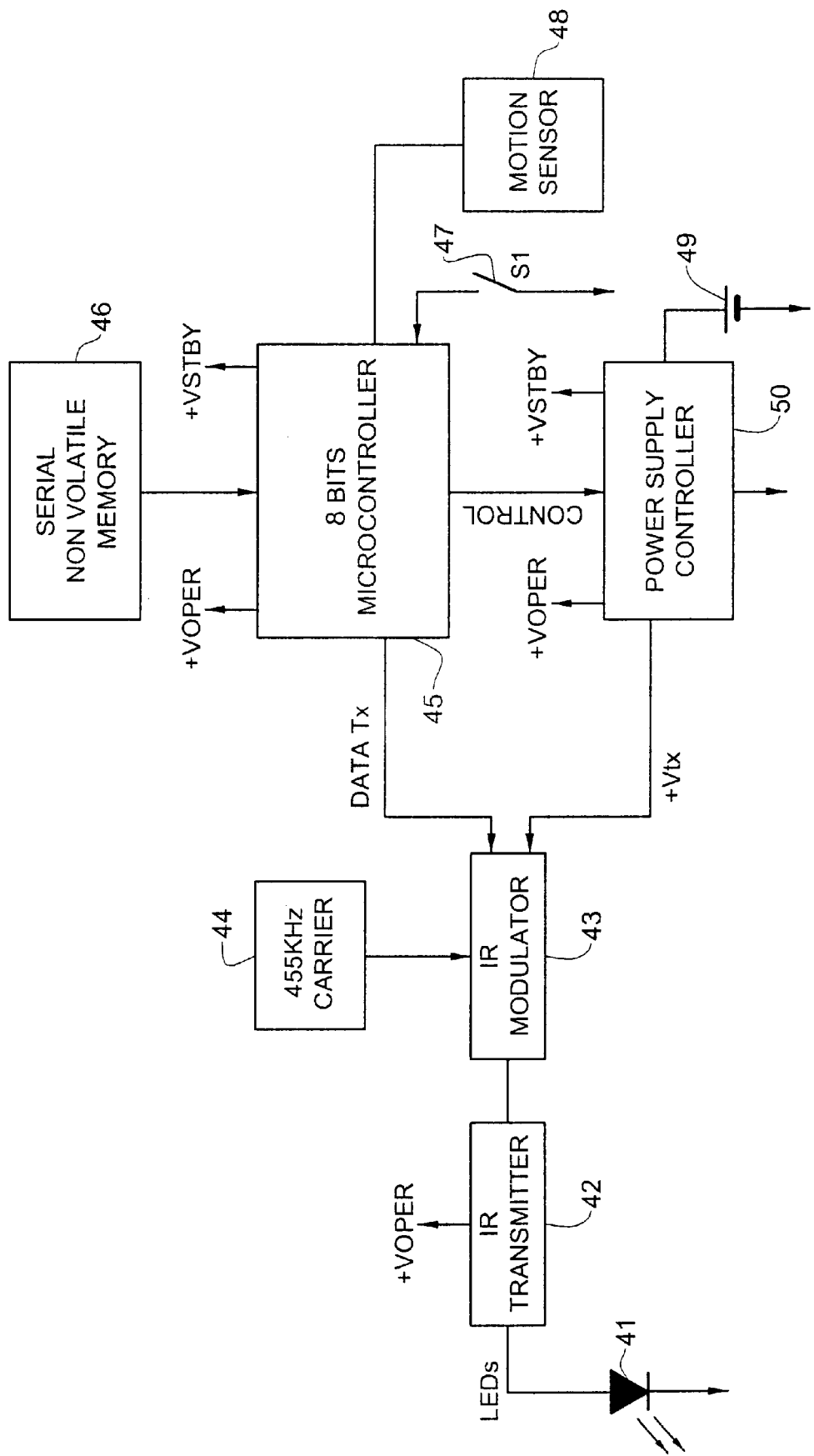
FIG. 4 is a block diagram showing schematically an IR badge for use in the IR/RF location system.

FIG. 4 shows a block diagram of a single mode, unidirectional IR badge depicted generally as 40 and including an array of LEDs 41 connected to an IR transmitter 42 for transmitting an IR signal to one of the IR readers 14, 15 and 16. The IR transmitter 42 is coupled to an IR modulator 43 for modulating the IR signal with a 455 KHz carrier 44. A micro-controller 45 is coupled to the IR modulator 43 and operates in accordance with a stored instruction set defining communications protocols allowing messages to be communicated between the badge and reader. The various communications protocols are described in detail below with particular reference to FIGS. 10 to 14 of the drawings. Coupled to the micro-controller 45 is a non-volatile memory 46 for storing a unique badge ID as well as other badge parameters. Likewise, at least one manual pushbutton switch 47 is coupled to the micro-controller 45 and serves as a location-dependent actuator button for allowing a respective command to be sent for alerting the processor 28 that the badge wearer requires some service at the badge's location. A motion sensor 48 is coupled to the micro-controller 45 for feeding thereto a motion signal when the badge is moved.

This signal causes the badge to transmit its data at a higher rate and prolongs battery life, since only relatively sparse transmission is required when the badge is stationary. The badge circuitry is powered by a 3 volt lithium battery 49 connected to the micro-controller 45 and the IR transmitter 42 via a power supply controller 50.

Figure 5:
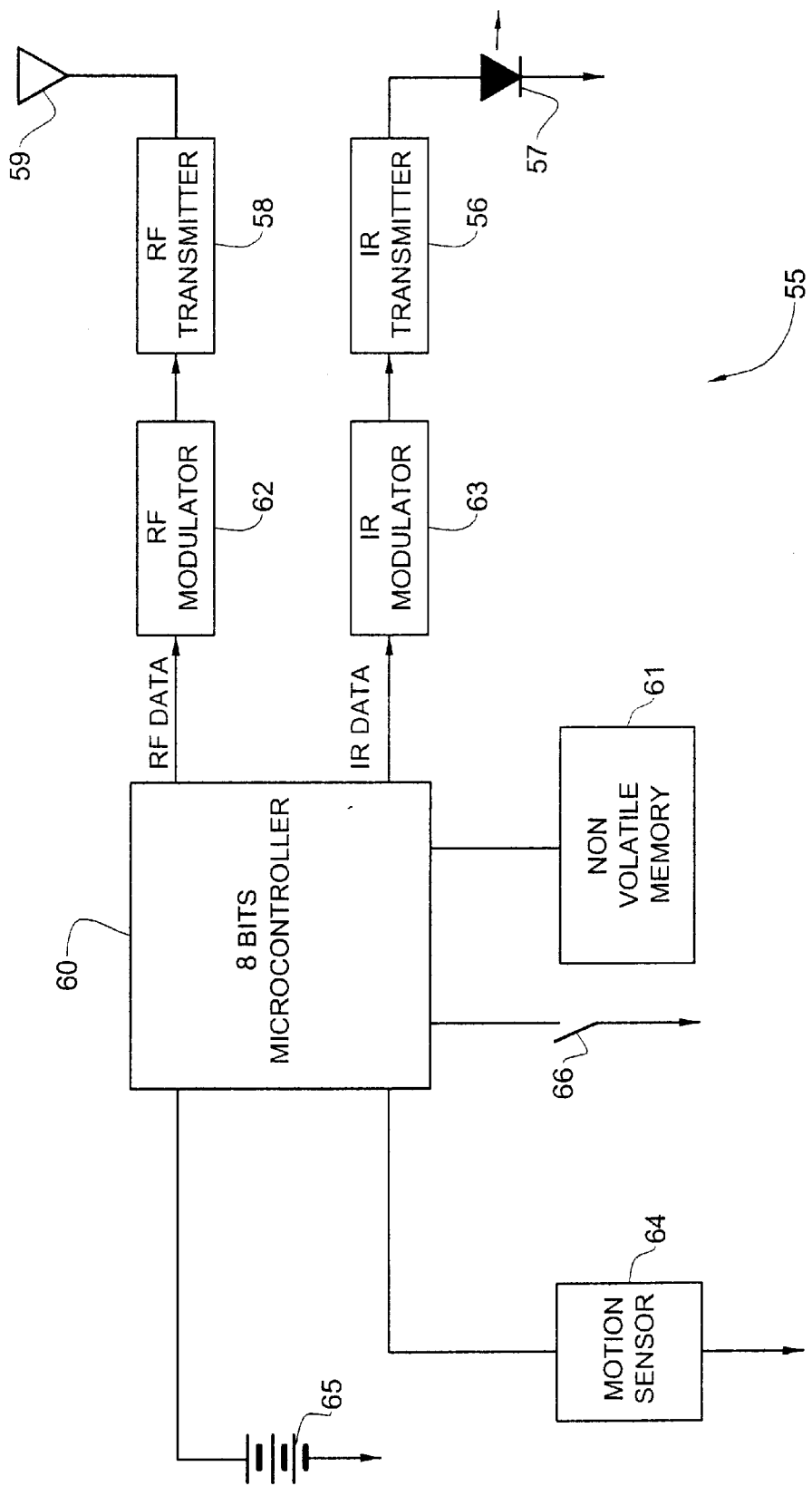
FIG. 5 is a block diagram showing schematically a dual-mode IR/RF unidirectional badge for use in the IR/RF location system.

FIG. 5 is a block diagram showing the principal functions of a dual mode, unidirectional IR/RF badge depicted generally as 55. The badge 55 includes an IR transmitter 56 for feeding an IR signal to an array of LEDs 57 as well as an RF transmitter 58 for feeding an RF signal to an RF microstrip antenna 59. A micro-controller 60 is responsive to the unique ID of the badge and the other badge parameters stored in a non-volatile memory 61 coupled thereto for feeding data to the RF transmitter 58 via an RF modulator 62. Likewise, the micro-controller 60 feeds data to the IR transmitter 56 via an IR modulator 63. An instruction set stored in an instruction memory of the micro-controller 60 defines communications protocols allowing messages to be communicated between the badge and reader. The various communications protocols are described in detail below with particular reference to FIGS. 10 to 14 of the drawings. A motion sensor 64 is coupled to the micro-controller 60 for feeding thereto a motion signal when the badge is moved. This signal causes the badge to transmit its data at a higher rate and prolongs battery life, since only relatively sparse transmission is required when the badge is stationary. The badge circuitry is powered by a 3 volt lithium battery 65 connected to the micro-controller 45. A manual pushbutton switch 66 is coupled to the micro-controller 60 and serves as a location-dependent actuator button for allowing a respective command to be sent for alerting the processor 28 that the badge wearer requires some service at the badge's location.

Figure 6:
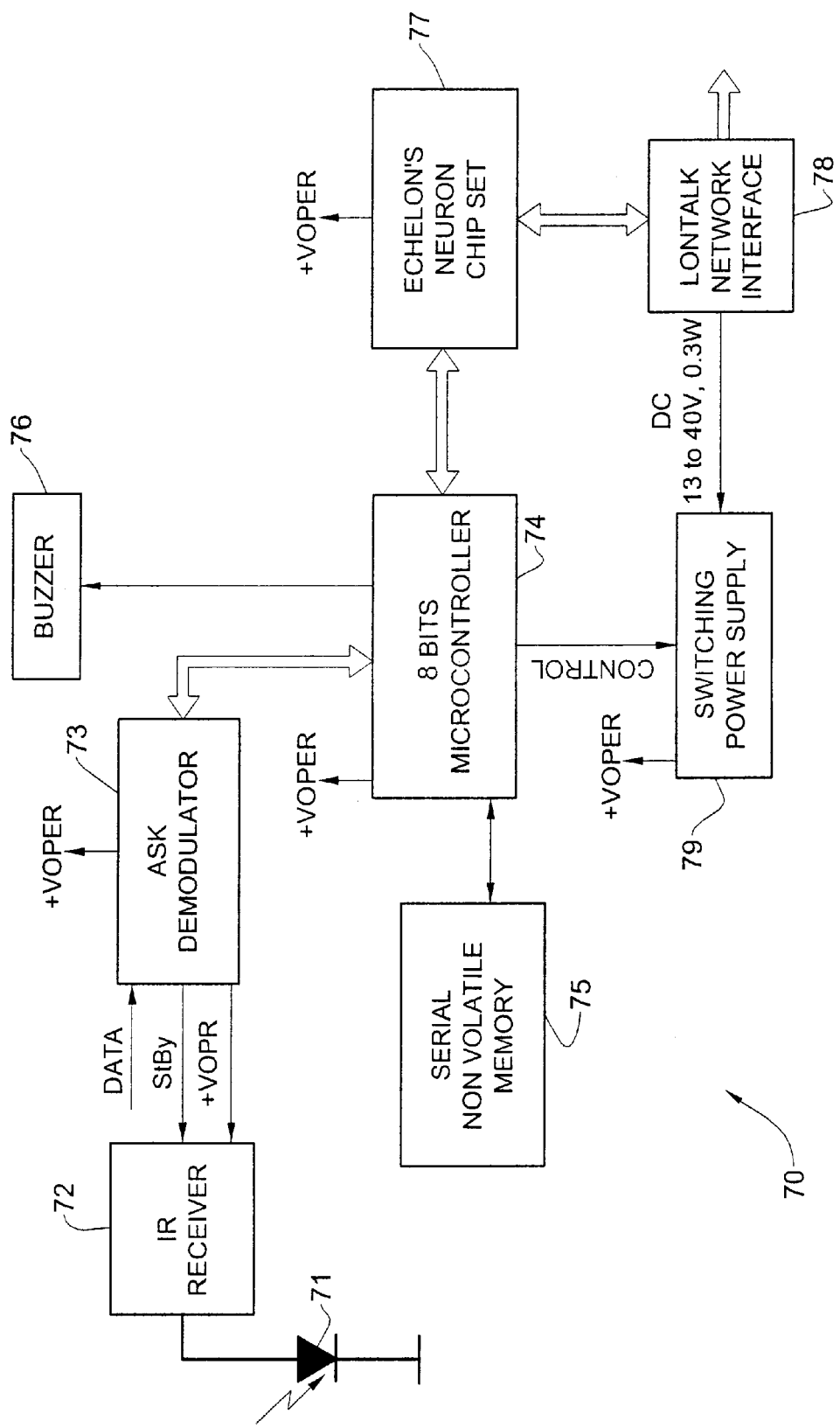
FIG. 6 is a block diagram showing schematically an IR Reader for use in the IR/RF location system.

FIG. 6 is a block diagram showing the principal functions of an IR Reader depicted generally as 70. An IR photodiode 71 is connected to an IR receiver 72 and feeds thereto a modulated IR signal transmitted thereto by a badge. The IR signal is demodulated by an Amplitude Shift Keying (ASK) demodulator 73, the demodulated signal being fed to a micro-controller 74 operating in accordance with an instruction set stored in a non-volatile memory 75. A buzzer 76 is connected to the micro-controller 74 to provide audible confirmation of reception by the reader of a badge transmission. By such means, for example, the reader can be audibly alerted when the badge wearer presses a panic button, or when a wire securing the badge to its wearer is cut. Also coupled to the micro-controller 74 is a network card 77, such as Echelon's Neuron chip set, which is connected to a LONTALK network interface 78 thereby allowing several readers to be networked to the server 25. The circuitry is powered by a switching power supply 79.

Figure 7:
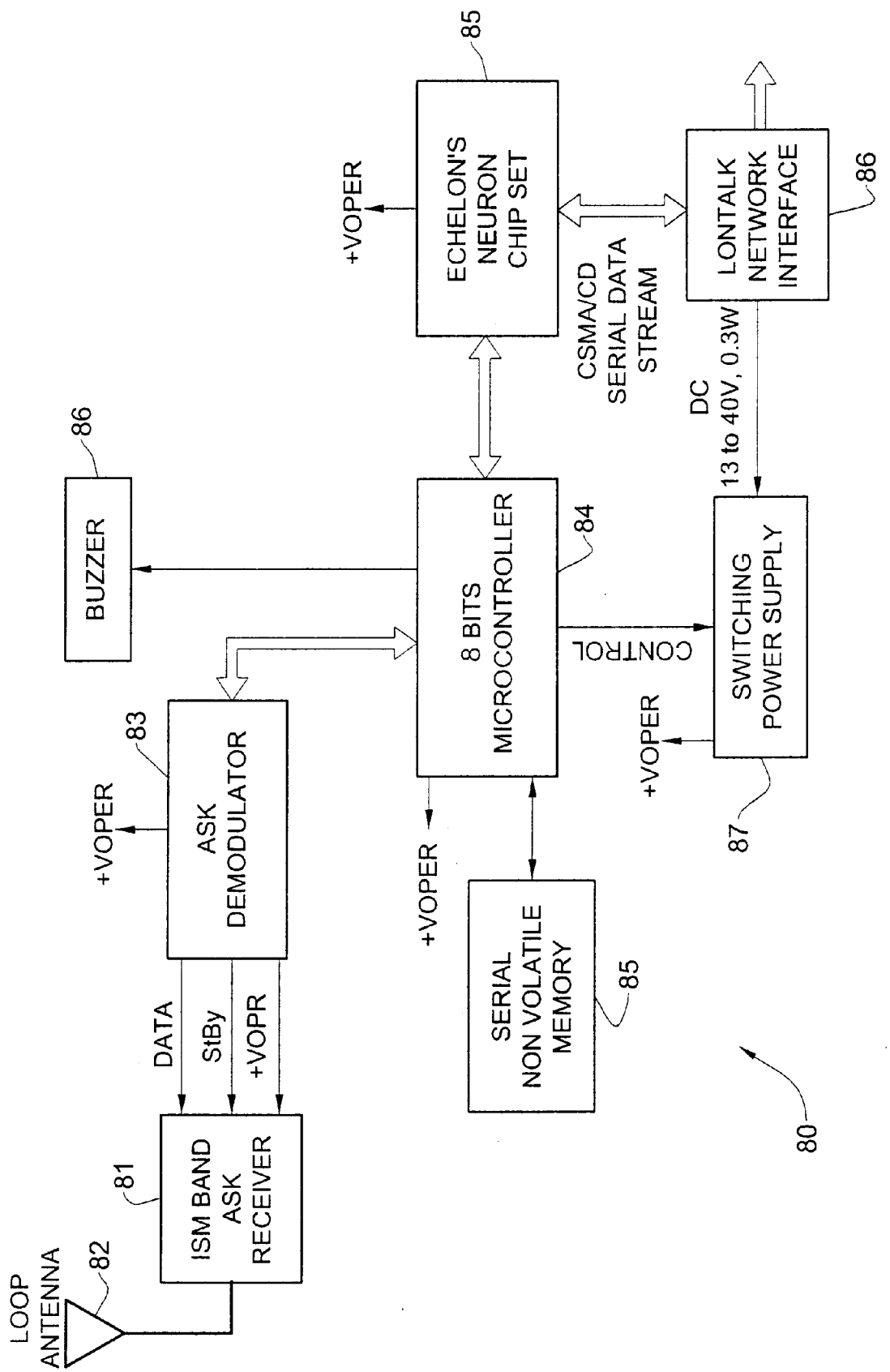
FIG. 7 is a block diagram showing schematically an RF Reader for use in the IR/RF location system.

FIG. 7 is a block diagram showing the principal functions of an RF Reader depicted generally as 80. An ISM band RF ASK receiver receives a modulated RF data signal via a loop antenna 81 in the industrial, scientific and medical band, thus obviating the need for FCC licensing. The modulated RF data signal is demodulated by an Amplitude Shift Keying (ASK) demodulator 83, the demodulated signal being fed to a micro-controller 84 operating in accordance with an instruction set stored in a non-volatile memory 85. A buzzer 86 is connected to the micro-controller 84 to provide audible confirmation of reception by the reader of a badge transmission. By such means, for example, the reader can be audibly alerted when the badge wearer presses a panic button, or when a wire securing the badge to its wearer is cut. Also coupled to the microcontroller 84 is a network card 85, such as Echelon's Neuron chip set, which is connected to a LONTALK network interface 86 thereby allowing several readers to be networked to the server 25. The circuitry is powered by a switching power supply 87.

Figure 8:
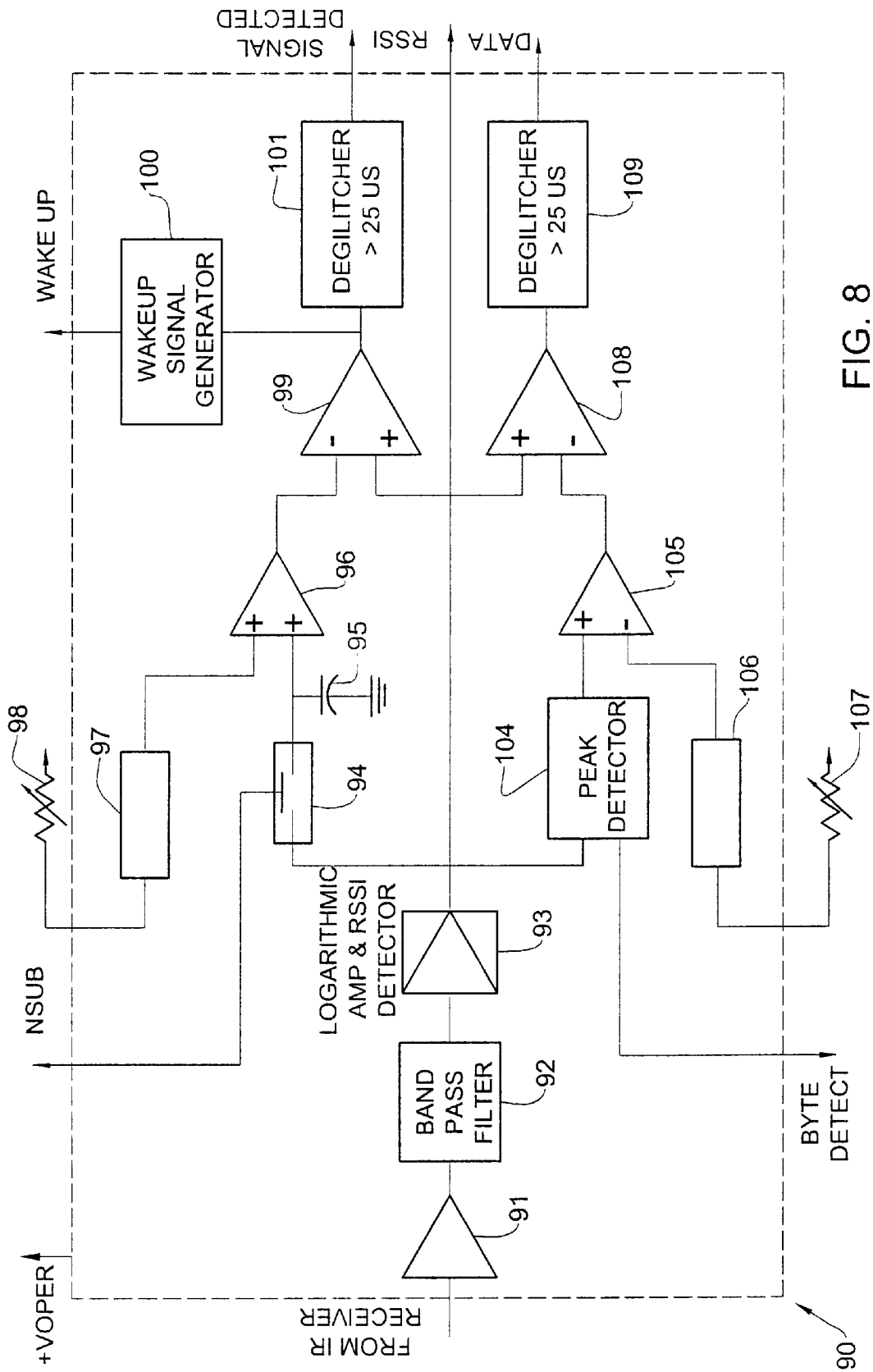
FIG. 8 is a block diagram showing schematically an IR Receiver Decoder for use in the IR/RF location system.

FIG. 8 shows in more detail the circuitry associated with an IR receiver decoder 90 used in the IR reader 70 shown functionally in FIG. 6. A similar circuit may likewise be employed in the badges 20 to 24 shown in FIG. 1 when bi-directional communication is required, as will be explained later with reference to FIG. 15. Thus, in both cases the 455 KHz ASK modulated IR signal received from the IR receiver 72 is fed to a low noise linear amplifier 91 operating at a basic frequency 455 KHz and having an output coupled to a band pass filter 92 having a bandwidth of 32 KHz. The resulting carrier signal is fed to the input of a logarithmic amplifier and Received Signal Strength Indicator (RSSI) 93 allowing the signal strength to be displayed in suitable form. The signal passed by the RSSI 93 includes both data and noise and it is obviously important to filter out the noise so that the IR receiver 72 does not receive false signals. Only those signals which are determined to be genuine data signals are demodulated so as to extract the data.

To this end there is coupled a noise subtract unit 94 an output of which is fed to a capacitor 95 operating as a noise integrator whose output is fed to a first input of a summing amplifier 96. A second input of the summing amplifier 96 is connected to a variable threshold generator 97 whose threshold may be set by a variable resistor 98 external to the IR receiver 72. The output of the summing amplifier 96, corresponding to the sum of the average noise and the noise threshold, is fed to the inverting input of a comparator 99 whose non-inverting input is fed to the RSSI signal produced by the amplifier and detector 93. The output of the comparator 99 may be fed to a "wake-up" signal generator 100. When the decoder 90 is used within an IR reader, which is energized through the national electricity supply, the "wake-up" signal generator 100 may be omitted, since its function is primarily to avoid battery wastage in the portable, battery-operated badges. The output of the comparator 99 is fed to a deglitcher 101 which suppresses any pulse whose time duration is less than 25 $\mu$s and thus constitutes spurious glitches rather than actual signal data. Thus, when a signal is detected at the output of the deglitcher 101, corresponding to an actual received signal, the corresponding data associated therewith is extracted and detected.

To this end, the RSSI signal is fed to a peak detector 104 which measures its peak value and feeds it to a first, summing input of a summing amplifier 105 having a second, subtracting input connected to a variable threshold generator 106 whose threshold may be set by a variable resistor 107 external to the IR receiver 72. The output of the summing amplifier 105, corresponding to the difference between the peak value of the RSSI signal and the threshold, is fed to the inverting input of a comparator 108 whose non-inverting input is fed to the RSSI signal produced by the amplifier and detector 93. The output of the comparator 108 is fed to a deglitcher 109 which suppresses any pulse whose time duration is less than 25 $\mu$s and thus constitutes spurious glitches rather than actual data. The waveforms associated with the decoded data, the RSSI signals are shown in FIGS. 13a and 13b of the drawings.

Figure 9:
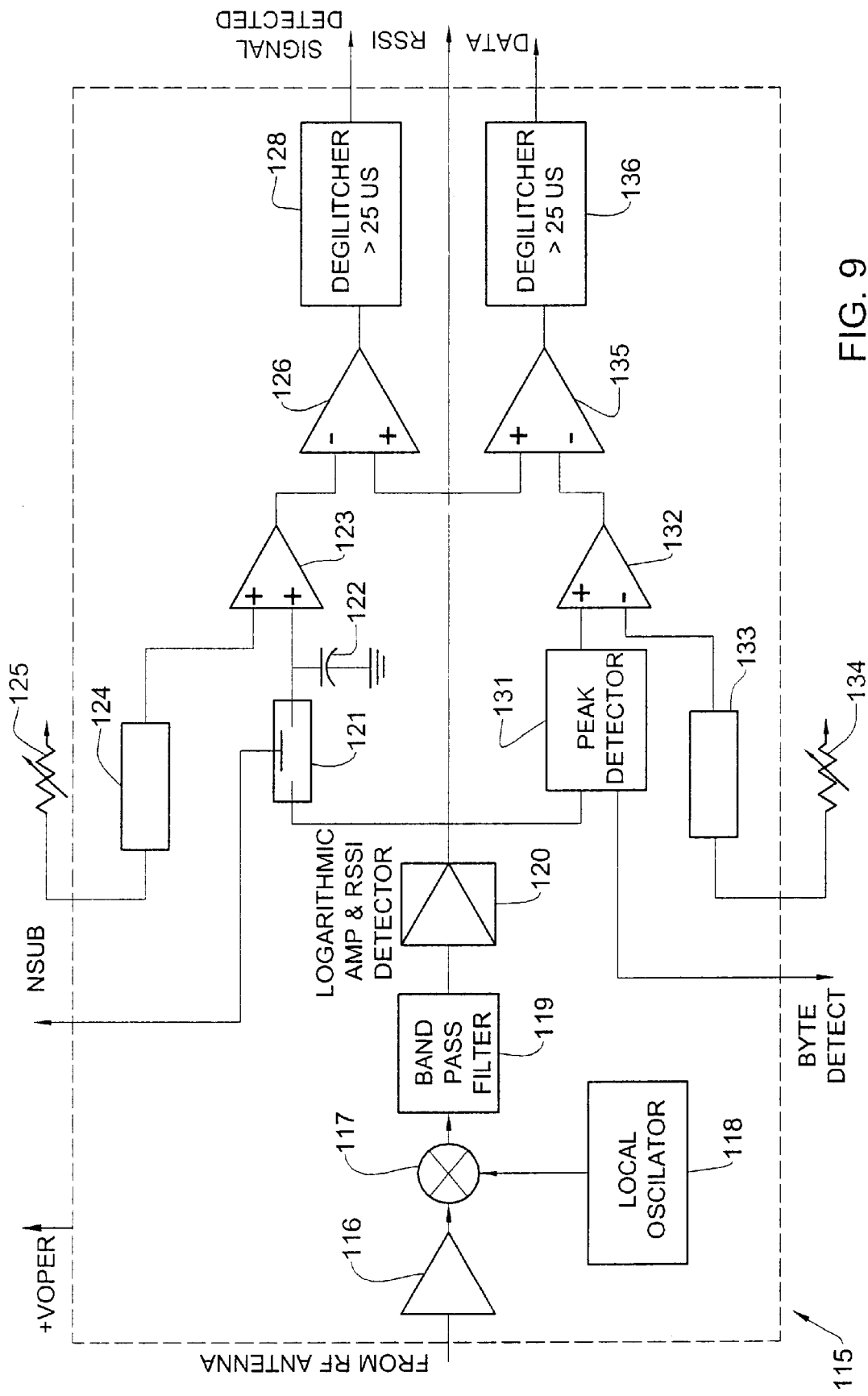
FIG. 9 is a block diagram showing schematically an RF Receiver Decoder for use in the IR/RF location system.

FIG. 9 shows in more detail similar circuitry associated with an RF receiver decoder 115 used in the RF reader 80 shown functionally in FIG. 7. The RF receiver decoder 115 is similar to the IR receiver decoder 90 described above with reference to FIG. 8, apart from the front end, as now described. The modulated RF signal received by the loop antenna 82 is fed to a low noise linear amplifier 116 operating at a basic reception frequency and having an output coupled to a mixer 117. An oscillator 118 feeds a signal having a frequency equal to the difference of received frequency less 10.7 MHz to the mixer 117, whose output is fed to a band pass filter 119 having a bandwidth of 150 KHz at a center frequency of 10.7 MHz. The resulting carrier signal is fed to the input of a logarithmic amplifier and Received Signal Strength Indicator (RSSI) 120 allowing the signal strength to be displayed in suitable form. The signal passed by the RSSI 120 includes both data and noise and it is obviously important to filter out the noise so that the IR receiver 72 does not receive false signals. Only those signals that are determined to be genuine data signals are demodulated so as to extract the data.

To this end there is coupled a noise subtract unit 121 an output of which is fed to a capacitor 122 operating as a noise integrator whose output is fed to a first input of a summing amplifier 123. A second input of the summing amplifier 123 is connected to a variable threshold generator 124 whose threshold may be set by a variable resistor 125 external to the RF receiver 81. The output of the summing amplifier 123, corresponding to the sum of the average noise and the noise threshold, is fed to the inverting input of a comparator 126 whose non-inverting input is fed to the RSSI signal produced by the amplifier and detector 120. The output of the comparator 126 is fed to a deglitcher 128 which suppresses any pulse whose time duration is less than 25 µs and thus constitutes spurious glitches rather than actual signal data. Thus, when a signal is detected at the output of the deglitcher 128, corresponding to an actual received signal, the corresponding data associated therewith is extracted and detected.

To this end, the RSSI signal is fed to a peak detector 131 which measures its peak value and feeds it to a first, summing input of a summing amplifier 132 having a second, subtracting input connected to a variable threshold generator 133 whose threshold may be set by a variable resistor 134 external to the RF receiver 81. The output of the summing amplifier 132, corresponding to the difference between the peak value of the RSSI signal and the threshold, is fed to the inverting input of a comparator 135 whose non-inverting input is fed to the RSSI signal produced by the amplifier and detector 120. The output of the comparator 135 is fed to a deglitcher 136 which suppresses any pulse whose time duration is less than 25 µs and thus constitutes spurious glitches rather than actual data.

FIGS. 10a to 10c show timing diagrams relating to the transmission of IR and RF signals by the badge prior to motion detection. When motion detection is enabled, a motion detect enable signal is set to ENABLED as shown in FIG. 10c and remains ENABLED for so long as no motion is detected. As shown in FIG. 10a, in the absence of motion, the IR transmitter 56 in the dual mode badge 55 shown in FIG. 5 transmits a short pulse of time duration equal to 2 ms. Thereafter, as shown in FIG. 10b following a time interval of 400 ms, the RF transmitter 58 also transmits a short pulse of time duration equal to 2 ms. The IR and RF signals serve as "I'm alive" signals showing that the badge is energized and functional. The period between adjacent pulses by each of the IR and RF transmitters is 60 s, during which period the transmitters are idle, thereby saving battery consumption.

FIGS. 11a to 11d show timing diagrams relating to the transmission of IR and RF signals by the badge following motion detection. Thus, as shown in FIGS. 11a and 11b during or following motion of the badge, a cycle of seven IR and RF pulses are transmitted having a random time interval between adjacent signals of 3 to 5 seconds. FIG. 11c shows a plurality of motion detect signals produced consequent to the badge's intermittent movement. As shown in FIG. 11d, the motion detect enable signal returns to the DISABLED state when the first intermittent movement of the badge ceases. Thereafter, it remains DISABLED until termination of the last RF pulse in the cycle, whereupon is goes back to the ENABLED state. This ensures that once motion has been detected, further motion of the badge during the seven signal cycle of between 21 to 35 seconds is ignored. Were this not the case, intermittent motion of the badge would result in interruptions of the cycle of seven signals thereby rendering the communications protocol unpredictable.

Owing to the very small time slot during which a stationary badge transmits as a proportion of the overall cycle between successive transmissions, the likelihood of two stationary badges attempting to transmit during the identical 2 ms period is negligible. When the badges move, the time interval between successive transmissions is randomly varied between 3 and 5 seconds. Thus, here too, the risk of two or more badges attempting to transmit within the same time slot may be sufficiently reduced. Obviously, conventional data collision techniques requiring re-transmission of data may be employed in the event that, notwithstanding efforts to the contrary, two different badges are transmitted simultaneously.

FIG. 12a shows the IR/RF modulation scheme employing on-off keying (00K) modulation of the 455 KHz pulse train constituting the modulated carrier transmitted by the reader. A high logic level constituting logic "1" is thus represented by an absence of data whereas a low logic level (logic "0") results in a modulated pulse being transmitted by the reader to the badge.

FIG. 12b shows an IR or RF signal transmitted by the badge which for an IR message comprises a 455 KHz carrier preamble and for an RF message comprises a UHF carrier preamble, both followed by a plurality of data words.

FIGS. 13a and 13c show timing diagrams of a data decoding circuit used in the IR receiver 72 of the Reader 70. In order to understand these diagrams, reference is again made to FIG. 8 showing a detail of the IR receiver decoder 140. The RSSI signal shown as 140 in FIG. 13a is taken from the output of a logarithmic amplifier thus accounting for its irregular shape. The average noise derived at the output of the noise integrator is shown in FIG. 13a as a noise floor is 141, whilst an upper noise limit 142 is shown as a 13.5 dB offset from the noise floor 141. The 13.5 dB offset is set by the noise threshold generator 97 and the external potentiometer 98 shown in FIG. 8. That is to say, the upper noise limit 142 defines the largest signal which could conceivably be noise: anything larger is accepted as genuine data. The upper noise limit 142 thus defines the level of the "wake up" signal 143 produced by the wake up generator shown in FIG. 8. For so long as the RSSI signal 140 is greater than the noise threshold 142, the "wake up" signal 143 is HIGH, and the data signal derived from the peak detected RSSI signal is demodulated to produce the pulse train shown as 144 in FIG. 13b. The pulse train 144 is derived by clipping the RSSI signal 140 by 6 dB, this being the peak threshold set by the threshold generator 106 and the external potentiometer 107 shown in FIG. 8 and shown as 145 in FIG. 13a. The threshold 145 is subtracted from the RSSI signal 140 by the summing amplifier 105 which operates as a subtractor.

FIGS. 14a to 14d show the effect of pressing the pushbutton switch 47 in the badge 40 shown functionally in FIG.

4 or of cutting an electrically conductive wire used to fasten the badge to an object or person. As shown in FIG. 14a, pressing the pushbutton switch 47 gives rise to a short negative pulse, whilst as shown in FIG. 14b, cutting the wire produces a continuous positive voltage level. As shown in FIGS. 14c and 14d, both give rise to transmission of an IR and RF pulse train, wherein there are transmitted four pulse, each having a width of 2 ms and a period of 400 ms. When the wire is cut, the badge subsequently transmits another pulse every 4 to 5 sec. Differentiation between "button press" and "wire cut" may be achieved by consideration of the polarity of the button press and wire cut signals shown in FIGS. 14a and 14b, respectively. Specifically, the button press signal returns to its original polarity whilst the wire cut signal is permanently inverted when the wire is cut. Thus, the initial transmission of four pulses in quick successive alerts the reader of a potential hazard, whilst the subsequent continuous, albeit less frequent, transmission owing to the a wire cut condition indicates a genuine hazard.

The description so far relates to a unidirectional badge as shown in FIG. 5, allowing for transmission only. In practice, it is often desirable to allow for reception of IR signals transmitted to the badge by the IR readers 14 to 16 (shown in FIG. 1).

Figure 15:
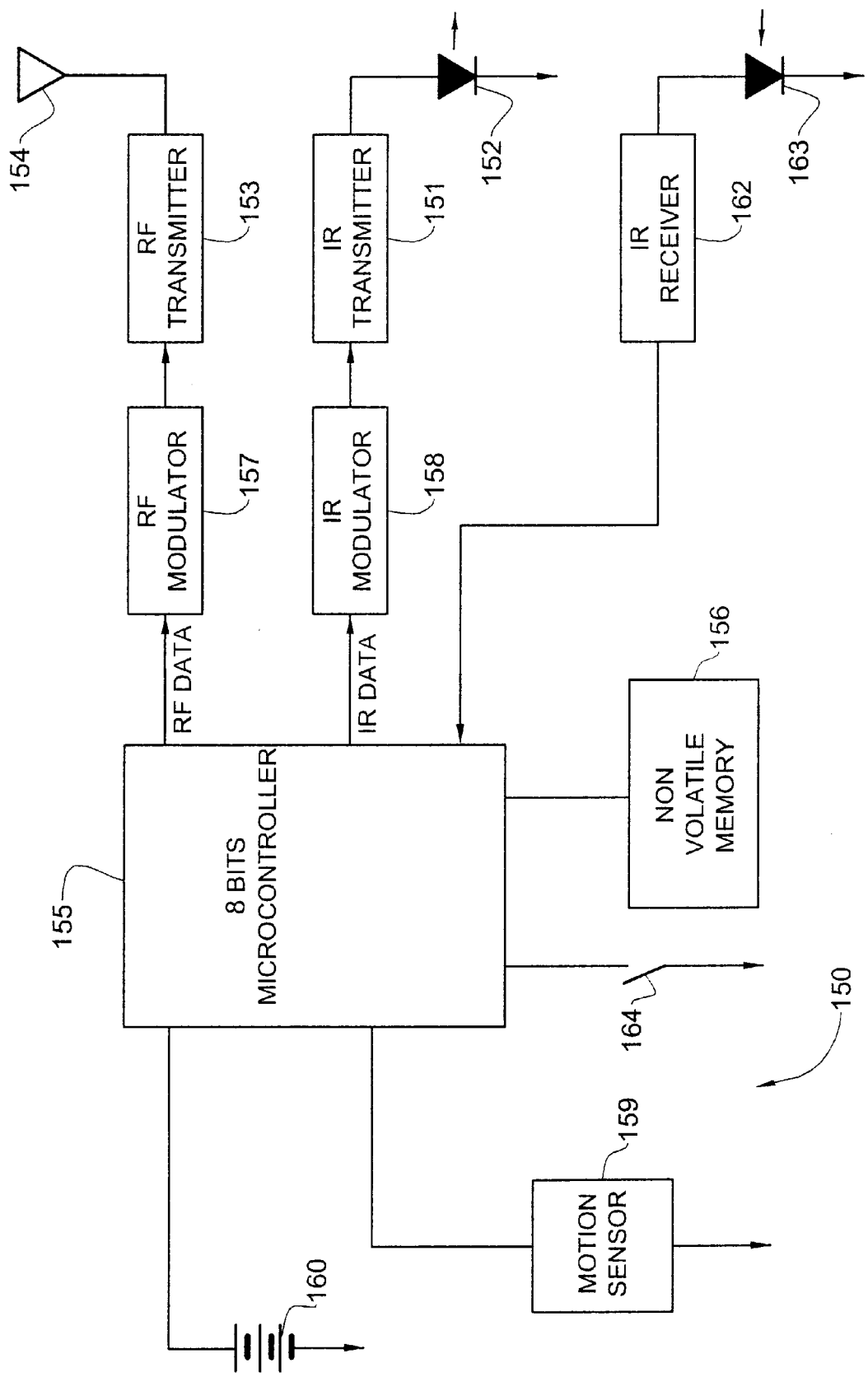
FIG. 15 is a block diagram showing schematically a dual-mode IR/RF bi-directional badge for use in the IR/RF location system.

FIG. 15 is a block diagram showing the principal functions of a dual mode, bi-directional IR/RF badge depicted generally as 150. The badge 150 includes an IR transmitter 151 for feeding an IR signal to an array of LEDs 152 as well as an RF transmitter 153 for feeding an RF signal to an RF microstrip antenna 154. A micro-controller 155 is responsive to an instruction set stored in a non-volatile memory 156 coupled thereto for feeding data to the RF transmitter 153 via an RF modulator 157. Likewise, the micro-controller 155 feeds data to the IR transmitter 151 via an IR modulator 158. The instruction set stored in the non-volatile memory 156 defines communications protocols allowing messages to be communicated between the badge and reader. The various communications protocols are described in detail above with particular reference to FIGS. 10 to 14 of the drawings. A motion sensor 159 is coupled to the micro-controller 155 for feeding thereto a motion signal when the badge is moved. The badge circuitry is powered by a 3 volt lithium battery 160 connected to the micro-controller 45. Also coupled to the micro-controller 155 is an IR receiver 162 connected to a photodiode 163 for receiving IR messages from one of the IR readers 14 to 16. The IR receiver 162 includes a decoder which may be identical to that provided in the IR readers and described in detail above with reference to FIG. 8 of the drawings. A manual pushbutton switch 164 is coupled to the micro-controller 155 and serves as a location-dependent actuator button for allowing a respective command to be sent for alerting the processor 28 that the badge wearer requires some service at the badge's location.

Figure 16:
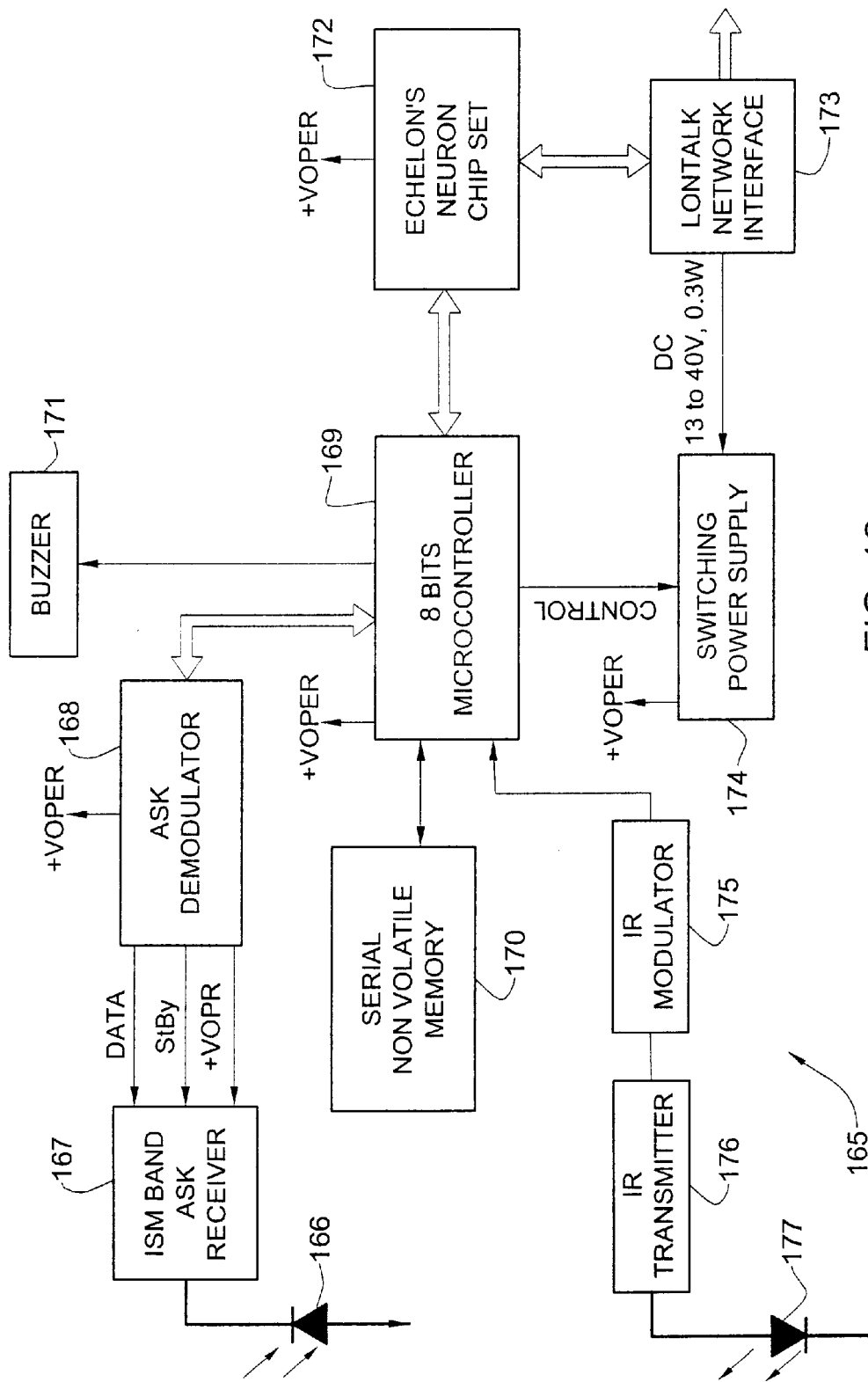
FIG. 16 is a block diagram showing schematically a bi-directional IR Reader for use in the IR/RF location system.

FIG. 16 is a block diagram showing the principal functions of a bi-directional IR Reader depicted generally as 165. An IR photodiode 166 is connected to an IR receiver 167 and feeds thereto a modulated IR signal transmitted thereto by a badge. The IR signal is demodulated by an Amplitude Shift Keying (ASK) demodulator 168, the demodulated signal being fed to a micro-controller 169 operating in accordance with an instruction set stored in a non-volatile memory 170. A buzzer 171 is connected to the micro-controller 169 to provide audible confirmation of reception by the reader of a badge transmission. By such means, for example, the reader can be audibly alerted when the badge wearer presses a panic button, or when a wire securing the badge to its wearer is cut. Also coupled to the micro-controller 169 is a network card 172, such as Echelon's Neuron chip set, which is connected to a LONTALK network interface 173 thereby allowing several readers to be networked to the server 25. The circuitry is powered by a switching power supply 174. In order to allow for data transmission to the badges, there is further coupled to the micro-controller 169 an IR modulator 175 for modulating data fed thereto by the micro-controller 169. The modulated signal is fed to an IR transmitter 176 having an array of IR LEDs 167 connected thereto.

Figure 17:
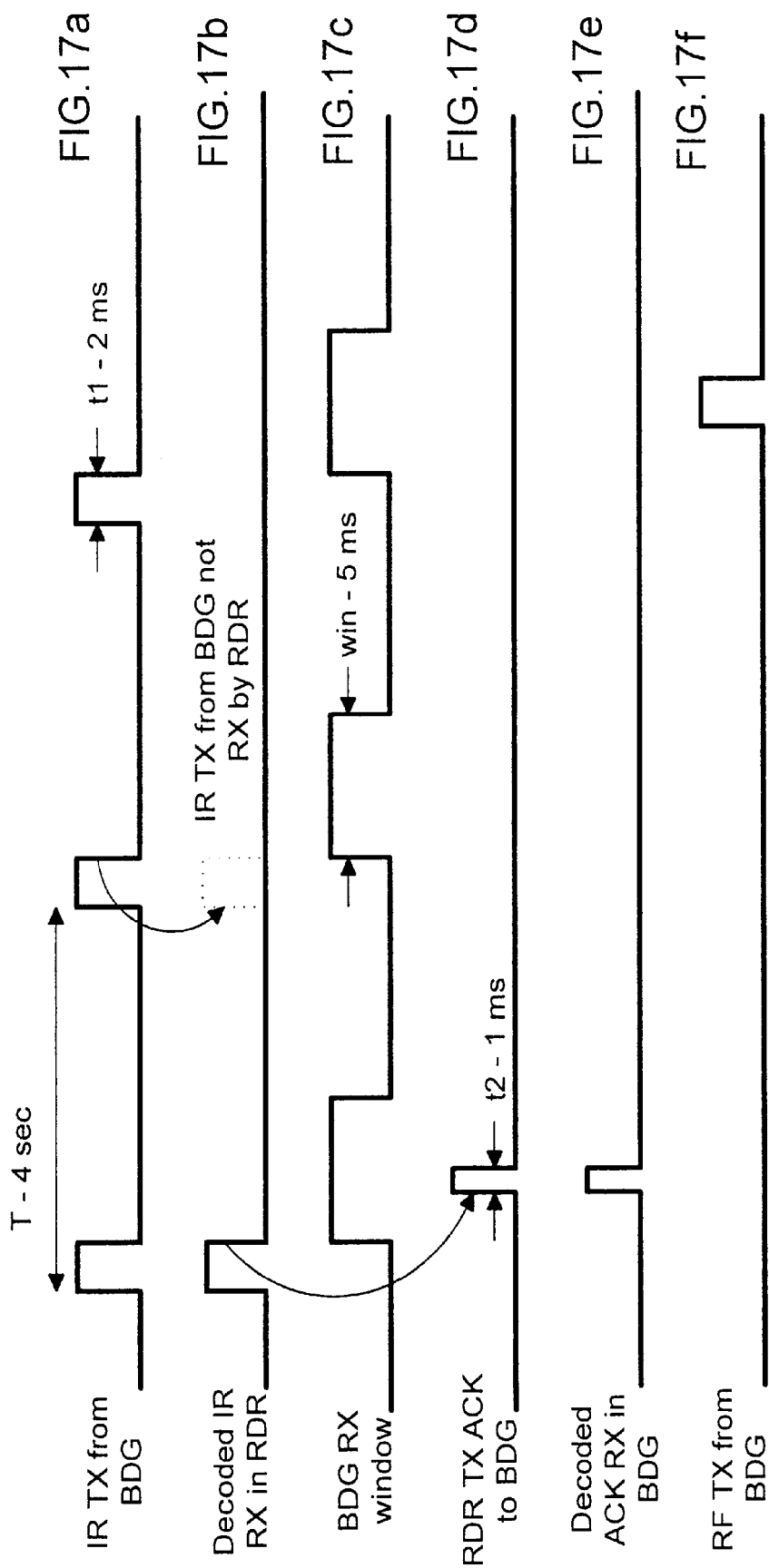
FIGS. 17a to 17f are timing diagrams of dual-mode IR/RF bi-directional operation of the badge.

FIGS. 17a to 17f show timing diagrams associated with data communication between a badge and reader. As shown in FIG. 17a, the badge is programmed to transmit a pulse having a width of 2 ms and a period of 4 s. FIG. 17b shows the corresponding signal received and decoded by the reader. Thus, the first pulse transmitted by the badge is shown as being also received and decoded by the reader. However, the second pulse transmitted by the badge is shown dotted in FIG. 17b implying that it is not received by the reader.

As shown in FIG. 17c, following transmission of a pulse by the badge, a "receive window" is opened having a duration of 5 ms for receiving therein a 1 ms acknowledge signal from the reader as shown in FIG. 17d. FIG. 17e shows the decoded acknowledge signal actually received by the badge. Referring back to FIGS. 17a to 17c, it will be noted that during the "receive window" following transmission of the second pulse by the badge in FIG. 17a, no signal is received by the reader. Therefore, an acknowledge signal is neither transmitted by the reader nor received by the badge, as shown in FIGS. 17d and 17e respectively. In the absence of receipt by the badge of an acknowledge signal, the badge now transmits a 2 ms RF signal to the reader as shown in FIG. 17f 400 ms after transmission of the next (i.e. third) IR pulse shown in FIG. 17a. The RF signal is received by the RF reader 17 shown in FIG. 1 and allows monitoring of the badge's location even when IR communication is ineffective.

Figure 18:
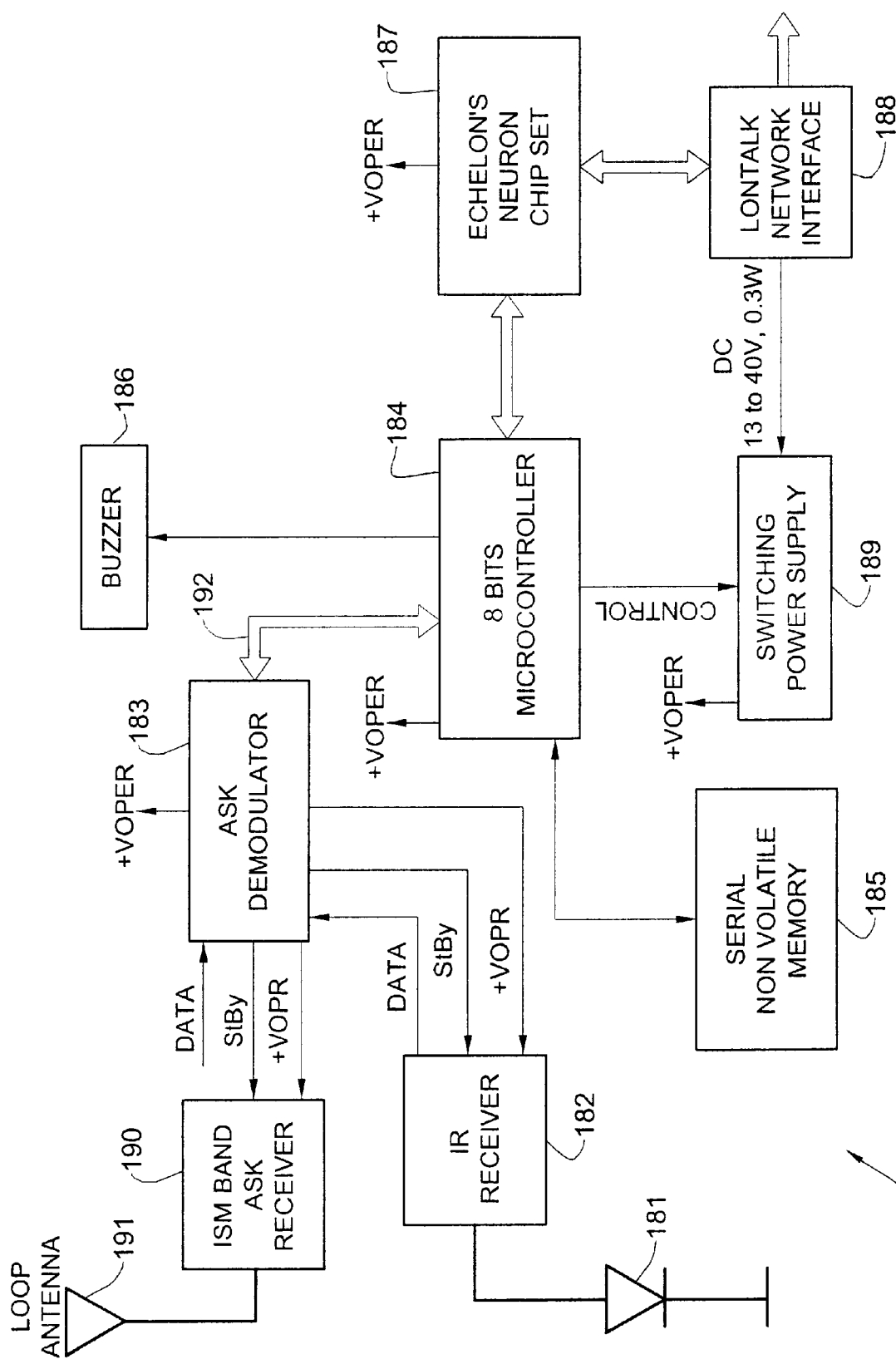
FIG. 18 is a block diagram showing schematically a bi-directional IR/RF Reader for use in the IR/RF location system.

FIG. 18 is a block diagram showing the principal functions of a dual mode bi-directional IR/RF Reader depicted generally as 180. An IR photodiode array 181 is connected to an IR receiver 182 and feeds thereto a modulated IR signal transmitted thereto by a badge. The IR signal is demodulated by an Amplitude Shift Keying (ASK) demodulator 183, the demodulated signal being fed to a micro-controller 184 operating in accordance with an instruction set stored in a non-volatile memory 185. A buzzer 186 is connected to the micro-controller 184 to provide audible confirmation of reception by the reader of a badge transmission. By such means, for example, the reader can be audibly alerted when the badge wearer presses a panic button, or when a wire securing the badge to its wearer is cut. Also coupled to the micro-controller 184 is a network card 187, such as Echelon's Neuron chip set, which is connected to a LONTALK network interface 188 thereby allowing several readers to be networked to the server 25. The circuitry is powered by a switching power supply 189. In order to allow for receipt of RF data transmitted by the badges, there is further coupled to the demodulator 183 an ISM Band ASK receiver 190 (constituting an RF receiver) for receiving RF data fed thereto via a loop antenna 191. The demodulator 183 thus feeds both IR and RF data along a bus 192, which constitutes an output connection commonly connected to the IR receiver 182 and the RF receiver 190. The bus 192 thus conveys both IR and RF data to the server 25 (shown in FIG. 1) via the micro-controller 184, the network card 187 and the network interface 188.

In the method claims that follow, alphabetic characters used to designate claim steps are provided for convenience only and do not imply any particular order of performing the steps.

What is claimed is:

1. A portable device including an RF transmitter mounted in conjunction with an IR transmitter for transmitting data by RF as well as by IR, and further including
an IR receiver for receiving an IR acknowledge signal, allowing a reader to establish location of the portable device as an enclosed zone in which an IR data signal transmitted by the portable device is received by the reader and allowing the reader to establish location of the portable device based on a measured signal strength of a received RF signal if no IR data signal is received within a predetermined time;
said RF transmitter being adapted to transmit only if the IR receiver does not receive the IR acknowledge signal within said predetermined time following transmission of the IR data signal by the IR transmitter.

2. The device according to claim 1, wherein:
the IR transmitter is adapted to transmit bursts of data packets having a low duty factor, and
the RF transmitter is adapted to transmit bursts of modified data packets following transmission by the IR transmitter.

3. The device according to claim 1, further including an IR receiver and a RF receiver for receiving infrared and RF data transmitted thereto by an IR transmitter and RF transmitter, respectively.

4. The device according to claim 1, further including a motion sensor responsive to a motion sensor enable signal for producing a motion detect signal upon movement of the device, and
being responsive to a change in the device from motionless to moving for transmitting from an initial transmission rate to a higher transmission rate, and vice versa.

5. The device according to claim 1, further including an electrically conductive wire for attaching the device to an object or person and wherein the IR transmitter and RF transmitter are responsive to the wire being cut for transmitting a modified IR message and a modified RF message, respectively.

6. The device according to claim 1, further including at least one actuator button and wherein the IR transmitter and RF transmitter are responsive to the at least one actuator button being actuated for transmitting a respective IR actuation signal and RF actuation signal.

7. The device according to claim 5, further including an actuator button and wherein:
(a) the IR transmitter is responsive to the actuator button being actuated for transmitting an IR actuation signal,
(b) the RF transmitter is responsive to the actuator button being actuated for transmitting an RF actuation signal,
(c) cutting the wire and actuating the actuator button produce mutually distinctive status signals, thereby allowing a reader receiving the status signals to determine a cause thereof.

8. A reader including an IR receiver and an RF receiver for respectively receiving IR and RF data signals from a portable device having a respective IR transmitter and a respective RF transmitter as well as a respective IR receiver for tracking and location thereof, and being responsive to an IR data signal transmitted by the IR transmitter in the portable device within an enclosed zone for establishing said enclosed zone as the location of the portable device and for determining the location of the portable device based on a measured signal strength of the received RF signal if no IR data signal is received within a predetermined time window;
said reader being responsive to said IR data signal for sending an IR acknowledge signal for receipt by the IR receiver in the portable device so as to allow the portable device to disable the RF transmitter and being responsive to the RF data signal transmitted by the RF transmitter in the portable device after expiry of said predetermined time window for locating and tracking the portable device.

9. The reader according to claim 8, wherein the IR receiver and the RF receiver are coupled to a common output for feeding the IR signals and RF signals together to a communication device coupled to said common output.

10. A system for locating and tracking a portable device, said system comprising a portable communication device and a plurality of readers;
the portable communication device including a battery operated RF transmitter mounted in conjunction with an IR transmitter and an IR receiver allowing RF data to be transmitted and IR data to be transmitted and received said RF transmitter being adapted to transmit only if an IR data signal transmitted by the IR transmitter in the portable communication device is not acknowledged by the reader within a predetermined time window following transmission of the IR data signal, and
at least some of the readers including:
an IR receiver for receiving an IR data signal transmitted thereto by the IR transmitter in the portable communication device within an enclosed zone and being responsive to said IR data signal for establishing said enclosed zone as the location of the portable communication device, and
an IR transmitter responsive to said IR data signal for transmitting an IR acknowledge signal to the portable communication device within said predetermined time window following transmission of the IR data signal by the portable communication device;
at least one of the readers including an RF receiver for receiving an RF signal transmitted thereto by the RF transmitter in the portable communication device if no IR signal is received by the IR receiver therein within said predetermined time window following transmission of an IR data signal by the IR transmitter therein, and
an RF signal location unit coupled to the RF receiver for determining the location of the portable communication device based on a measured signal strength of the received RF signal.

11. The system according to claim 10, wherein:
the IR transmitter in the portable communication device is adapted to transmit bursts of data packets having a low duty factor, and
the RF transmitter in the portable communication device is adapted to transmit bursts of modified data packets following transmission by the IR transmitter.

12. The system according to claim 10, wherein each of the readers further includes:
an IR transmitter for transmitting IR data to the portable data communication device.

13. The system according to claim 10, wherein each of the readers further includes:
an output connection commonly connected to the IR receiver and the RF receiver for feeding the IR data and RF data together to a communication device coupled to said output connection.

14. The system according to claim 10, wherein each of the portable communication devices further includes a motion sensor responsive to a motion sensor enable signal for producing a motion detect signal upon movement of the device.

15. The system according to claim 14, wherein at least one of the readers is responsive to a change in the portable communication device from motionless to moving for transmitting from an initial transmission rate to a higher transmission rate, and vice versa.

16. The system according to claim 10, wherein the portable communication device further includes an electrically conductive wire for attaching the portable communication device to an object or person and wherein the IR transmitter and the RF transmitter therein are responsive to the wire being cut for transmitting a modified IR message and a modified RF message, respectively.

17. The system according to claim 10, wherein the portable communication device further includes at least one actuator button and wherein the IR transmitter and the RF transmitter therein are responsive to the at least one actuator button being actuated for transmitting respective IR and RF actuation signals.

18. The system according to claim 16, wherein the portable communication device further includes at least one an actuator button and wherein:
   (a) the IR transmitter therein is responsive to the actuator button being actuated for transmitting an IR actuation signal,
   (b) the RF transmitter therein is responsive to the actuator button being actuated for transmitting an RF actuation signal,
   (c) cutting the wire and actuating the actuator button produce mutually distinctive status signals, thereby allowing one of the readers receiving the status signal to determine a cause thereof.

19. A method for using the system according to claim 10 to locate and track a portable communication device, the method comprising the steps of:
   (a) mounting each of the readers in a respective enclosed space so that IR data received or transmitted by each of the readers is confined to the respective closed space,
   (b) the IR transmitter in the portable communication device transmitting successive IR data pulses for reception by one of the IR readers,
   (c) upon receipt of an IR data pulse by an IR receiver in one of the readers, said IR receiver sending an acknowledge signal to the portable communication device for reception by the IR receiver therein within a predetermined time window following transmission of said IR data pulse,
   (d) upon no acknowledge signal being received by the IR receiver within the portable communication device within said time window, the RF transmitter in the portable communication device transmitting successive RF data pulses for reception by an RF receiver in one of the readers, and
   (e) determining the location of the portable communication device from the respective closed space in which data transmitted thereby is received by the reader.

20. A method for using the system according to claim 10 to locate and track a portable communication device, the method comprising the steps of:
   (a) mounting each of the readers in an open space so that IR data transmitted by the portable communication device may be received by more than one reader,
   (b) the IR transmitter in the portable communication device transmitting successive IR data pulses for reception by one or more of the IR readers,
   (c) upon receipt of an IR data pulse by the respective IR receiver in one or more of the readers determining a respective signal strength of each signal received by the respective IR receiver, and
   (d) computing a location of the device based on the received signal strengths.

21. A method for communicating between a portable communication device including a battery-operated RF transmitter mounted in conjunction with an IR transmitter and an IR receiver and one or more IR readers and an RF reader, said method comprising the steps of:
   (a) the IR transmitter transmitting successive IR data pulses for reception by one of the IR readers,
   (b) upon receipt of an IR data pulse by one of the IR readers, said IR reader sending an acknowledge signal to the portable communication device for reception by the IR receiver therein within a predetermined time window following transmission of said IR data pulse,
   (c) upon said acknowledge signal being received by the IR receiver within the portable communication device within said time window, the RF transmitter in the portable communication device being disabled,
   (d) upon no acknowledge signal being received by the IR receiver within the portable communication device within said time window, the RF transmitter transmitting successive RF data pulses for reception by the RF reader, and
   (e) repeating steps (a) to (d) in respect of subsequent data packets transmitted by the portable communication device.

22. The method according to claim 21, further including the steps of:
   (d) determining a respective signal strength of each signal received by the IR and RF receivers, and
   (e) computing a location of the device based on the received signal strengths.

23. A reader for receiving IR and RF signals from a portable device for tracking and location thereof, said reader including an IR transmitter allowing data to be transmitted by IR and an IR receiver and a RF receiver for receiving infrared and RF data transmitted thereto by an IR transmitter and RF transmitter, respectively and being responsive to the IR signal being transmitted within an enclosed zone for establishing said enclosed zone as the location of the portable device and for determining the location of the portable device based on a measured signal strength of the received RF signal if no IR signal is received within a predetermined time.

24. A method for locating and tracking a portable communication device having an IR transmitter and an IR receiver and an RF receiver using a plurality of readers each having an IR transmitter and an IR receiver and each having an RF receiver, the method comprising the steps of:
   (a) mounting each of the readers in a respective enclosed space so that IR data received or transmitted by each of the readers is confined to the respective closed space,
   (b) the IR transmitter in the portable communication device transmitting successive IR data pulses for reception by the respective IR receiver in one of the readers,
   (c) upon receipt of an IR data pulse by an IR receiver in one of the readers, said IR receiver sending an acknowledge signal to the portable communication device for reception by the IR receiver therein within a predetermined time window following transmission of said IR data pulse, (d) upon no acknowledge signal being received by the IR receiver within the portable communication device within said time window, the RF transmitter in the portable communication device transmitting successive RF data pulses for reception by the RF receiver in one of the readers, (e) determining the location of the portable communication device from the respective closed space in which data transmitted thereby is received by the reader, and (f) repeating steps (a) to (e) in respect of subsequent data packets transmitted by the portable communication device.

25. A method for locating and tracking a portable communication device having an IR transmitter and an IR receiver and an RF transmitter using a plurality of readers each having IR transmitter and an IR receiver and each having an RF receiver, the method comprising the steps of:

(a) mounting each of the readers in an open space so that IR data transmitted by the portable communication device may be received by more than one reader, (b) the IR transmitter in the portable communication device transmitting successive IR data pulses for reception by one or more of the IR receivers in the respective readers, (c) upon receipt of an IR data pulse by the respective IR receiver in one or more of the readers determining a respective signal strength of each signal received by the respective IR receiver, (d) computing a location of the device based on the received signal strengths, and (e) repeating steps (a) to (d) in respect of subsequent data packets transmitted by the portable communication device.

* * * * *